United States Patent
Bortolo et al.

(10) Patent No.: US 9,885,069 B2
(45) Date of Patent: Feb. 6, 2018

(54) PROCESS FOR THE PRODUCTION OF LIPIDS FROM BIOMASS

(71) Applicant: ENI S.P.A., Rome (IT)

(72) Inventors: Rossella Bortolo, Novara (IT); Roberta Miglio, Olleggio Novara (IT); Daniela Cucchetti, Cuggiono Milano (IT)

(73) Assignee: Eni S.p.A., Rome (IT)

( * ) Notice: Subject to any disclaimer, the term of this patent is extended or adjusted under 35 U.S.C. 154(b) by 220 days.

(21) Appl. No.: 14/650,667

(22) PCT Filed: Dec. 23, 2013

(86) PCT No.: PCT/EP2013/077940
§ 371 (c)(1),
(2) Date: Jun. 9, 2015

(87) PCT Pub. No.: WO2014/102254
PCT Pub. Date: Jul. 3, 2014

(65) Prior Publication Data
US 2015/0299746 A1    Oct. 22, 2015

(30) Foreign Application Priority Data
Dec. 28, 2012 (IT) .............................. MI2012A2249

(51) Int. Cl.
| | | |
|---|---|---|
| C12P 7/64 | (2006.01) | |
| C11B 1/02 | (2006.01) | |
| C11B 1/10 | (2006.01) | |
| C12N 1/16 | (2006.01) | |
| C11B 3/00 | (2006.01) | |

(52) U.S. Cl.
CPC ................ *C12P 7/649* (2013.01); *C11B 1/02* (2013.01); *C11B 1/10* (2013.01); *C11B 3/001* (2013.01); *C12N 1/16* (2013.01); *C12P 7/6463* (2013.01); *C12P 2203/00* (2013.01); *Y02E 50/13* (2013.01)

(58) Field of Classification Search
None
See application file for complete search history.

(56) References Cited

U.S. PATENT DOCUMENTS

| | | | | |
|---|---|---|---|---|
| 4,888,189 A | * | 12/1989 | Gnekow | .............. C12G 3/085 210/652 |
| 5,628,830 A | | 5/1997 | Brink | |
| 5,916,780 A | | 6/1999 | Foody et al. | |
| 6,090,595 A | | 7/2000 | Foody et al. | |
| 6,596,521 B1 | * | 7/2003 | Chang | ...................... C12P 7/40 435/136 |
| 2008/0102176 A1 | | 5/2008 | Wu | |
| 2011/0086386 A1 | | 4/2011 | Czartoski et al. | |

FOREIGN PATENT DOCUMENTS

| | | |
|---|---|---|
| EP | 1728844 | 12/2006 |
| WO | WO2009063138 | 5/2009 |
| WO | WO2009108773 | 9/2009 |
| WO | WO2010069516 | 12/2009 |
| WO | WO2010069583 | 12/2009 |
| WO | WO2010046051 | 4/2010 |
| WO | WO2012042544 | 9/2010 |
| WO | WO2010149859 | 12/2010 |
| WO | WO2012052368 | 4/2012 |

OTHER PUBLICATIONS

Yousuf. "Biodiesel from lignocellulosic biomass—Prospects and challenges," Waste Management, vol. 32, No. 11, Nov. 1, 2012, pp. 2061-2067.
Dai et al. "Biodiesel generation from oleaginous yeast Rhodotorula glutinis with xylose assimilating capacity", published in "African Journal of Biotechnology" (2007), vol. 6 (18), pp. 2130-2134.
Humbrid D. et al., Technical Report Nrel/Tp-5100-47764 (May 2011).
Knight, et al. "Chemical Basis of the Sulpho-phospho-vanillin Reaction for Estimating Total Serum Lipids", "Clinical Chemistry" (1972), vol. 18, No. 3, pp. 199-202.
International Search Report and Written Opinion dated May 20, 2014 for PCT/EP2013/077940.

* cited by examiner

*Primary Examiner* — Thane Underdahl (74) *Attorney, Agent, or Firm* — Abel Law Group LLP (57) ABSTRACT

Process for the production of lipids from biomass including at least one polysaccharide, which comprises fermentation of a biomass hydrolysate using an oleaginous microorganism and separation of oleaginous cellular biomass comprising lipids. An aqueous fraction obtained by reverse osmosis of a spent fermentation broth is recycled as a feed for growth of the oleaginous microorganism. The lipids thus obtained can be advantageously used in the production of biodiesel or green diesel which can be used as such, or in a mixture with other automotive fuels.

17 Claims, 1 Drawing Sheet

PROCESS FOR THE PRODUCTION OF LIPIDS FROM BIOMASS

The present invention relates to a process for the production of lipids from biomass including at least one polysaccharide.

More specifically, the present invention relates to a process for the production of lipids from biomass including at least one polysaccharide, which comprises subjecting said biomass including at least one polysaccharide to hydrolysis obtaining a mixture comprising a first solid phase and a first aqueous phase, preparing an inoculum comprising at least one oleaginous microorganism in a first fermentation device obtaining a first fermentation broth, feeding said first aqueous phase and said first fermentation broth to a second fermentation device obtaining a second fermentation broth, subjecting said second fermentation broth to separation obtaining an aqueous suspension of oleaginous cellular biomass comprising lipids and a second aqueous phase, subjecting said second aqueous phase to reverse osmosis obtaining a permeate and a retentate, feeding said retentate to said first fermentation device or to said second fermentation device.

The lipids thus obtained can be advantageously used in the production of biodiesel or green diesel which can be used as such, or in a mixture with other automotive fuels.

Generally speaking, a biomass is any substance with an organic, vegetable or animal matrix, which can be destined for energy purposes, for example, as raw material for the production of biofuels, or of components which can be added to fuels. Biomass can therefore form a renewable energy source as an alternative to traditional raw materials of a fossil origin, normally used in the production of fuels. For this purpose, lignocellulosic biomass is particularly useful.

The production of sugars from biomass, in particular from lignocellulosic biomass, is known in the art.

Lignocellulosic biomass is a complex structure comprising three main components: cellulose, hemicellulose and lignin. Their relative quantities vary according to the type of lignocellulosic biomass used. In the case of plants, for example, said quantities vary according to the species and to the age of the plant.

Cellulose is the greatest constituent of lignocellulosic biomass and is generally present in quantities ranging from 30% by weight to 60% by weight with respect to the total weight of the lignocellulosic biomass. Cellulose consists of glucose molecules (from about 500 to 10,000 units) bound to each other through a β-1,4 glucoside bond. The establishment of hydrogen bonds between the chains causes the formation of crystalline domains which give resistance and elasticity to vegetal fibres. In nature, it can only be found in its pure state in annual plants such as cotton and flax, whereas in ligneous plants it is always accompanied by hemicellulose and lignin.

Hemicellulose which is generally present in a quantity ranging from 10% by weight to 40% by weight with respect to the total weight of the lignocellulosic biomass appears as a mixed polymer, relatively short (from 10 to 200 molecules) and branched, composed of both sugars with six carbon atoms (glucose, mannose, galactose) and also sugars with five carbon atoms (xylose, arabinose). Some important properties of vegetal fibres are due to the presence of hemicellulose, of which the main property is that of favouring the imbibition of said vegetal fibres, when water is present, causing their swelling. Hemicellulose also has adhesive properties and therefore tends to harden or develop a horny consistency, with the consequence that said vegetal fibres become rigid and are imbibed more slowly.

Lignin is generally present in a quantity ranging from 10% by weight to 30% by weight with respect to the total weight of the lignocellulosic biomass. Its main function consists in binding and cementing the various vegetal fibres with each other giving the plant compactness and resistance and also provides protection against insects, pathogen agents, lesions and ultraviolet light. It is mainly used as fuel but is also currently widely used in industry as a dispersing agent, hardener, emulsifying agent, for plastic laminates, cartons and rubber end-products. It can also be chemically treated to produce aromatic compounds, of the vanillin, syringaldehyde, p-hydroxybenzaldehyde type, which can be used in pharmaceutical chemistry, or in the cosmetic and food industry.

In order to optimize the transformation of lignocellulosic biomass into products for energy use, subjecting said lignocellulosic biomass to a preliminary treatment to separate the lignin and to hydrolyze the cellulose and hemicellulose to simple sugars, such as, for example, glucose and xylose, is known. Said sugars can therefore be used as carbon sources in fermentation processes in the presence of microorganisms for the production of alcohols and/or of lipids.

International patent application WO 2009/108773, for example, describes a method for the pre-treatment of a lignocellulosic biomass which comprises: pre-treating the lignocellulosic biomass in a first pressurized reactor, wherein the lignocellulosic biomass is subjected to hydrolysis; discharging the lignocellulosic biomass from said first pressurized reactor and sending it to a pressurized sealing device having a first pressurized coupling connected to the discharge outlet of said first pressurized reactor; maintaining a vapour phase in said first pressurized reactor by the injection of vapour into the same, wherein the vapour injected provides the lignocellulosic biomass with thermal energy; washing the lignocellulosic biomass in a region downstream of said first pressurized reactor or of said pressurized sealing device; discharging a liquid comprising dissolved hemicellulose extracted from the lignocellulosic biomass from said first pressurized reactor or from said pressurized sealing device; discharging the lignocellulosic biomass from said pressurized sealing device through a second pressurized coupling into a second pressurized reactor, wherein the lignocellulosic biomass is kept at a higher pressure with respect to that of said first pressurized reactor; infusing the cells of the lignocellulosic biomass with steam or water vapour in said second pressurized reactor by the injection of steam or water vapour into said second pressurized reactor; rapidly releasing the pressure applied to the lignocellulosic biomass infused with water so as to cause an expansion of the vapour (steam explosion) in the cells of the lignocellulosic biomass and purifying the lignocellulosic biomass. Said method allows sugars to be obtained, which can be used for the production of alcohols (e.g., ethanol).

International patent application WO 2012/042544 describes a biomass composition comprising a solid, a liquid, a quantity of $C_5$ sugars based on the quantity of arabinans and xylans, and monomers, dimers, oligomers and polymers of arabinose and xylose contained in the liquid and in the solid of the composition, a quantity of $C_6$ sugars based on the quantity of glucan which comprises monomers, dimers, oligomers and polymers of the glucan contained in the liquid and in the solid of the composition and furfural, wherein the composition is also characterized in that for 24 hours it has an accessibility of at least 30% to hydrolytic enzymes. Said composition is obtained by means of steam explosion. The sugars obtained after enzymatic hydrolysis, can be used for the production of ethanol.

International patent application WO 2009/063138 describes a method for producing lipids or mixtures of lipids from organic material comprising a polysaccharide selected from the group comprising cellulose, hemicellulose, starch, all of these or mixtures thereof, or products deriving from their degradation or a polysaccharide not containing starch (non-starch polysaccharide), characterized in that it comprises: (a) treating the organic material with a substance selected from the group comprising (i) water, (ii) acid, and (iii) alkalis, and subsequently separating the precipitate and the filtrate obtained, and subjecting the precipitate obtained from said treatment to mechanical or thermo-mechanical granulation, as such or in the presence of water, acids or alkalis, and separating the precipitate and the filtrate obtained and, alternatively, subjecting the precipitate again, once or various times, to the treatment indicated under items (i), (ii) or (iii) and/or to granulation, and (b) putting a microorganism, capable of producing lipids, in contact with the filtrate thus obtained or with the various filtrates obtained or with the precipitate, or with any of their combinations and, optionally, with the organic material, in a culture medium, whereby the cells of the microorganism begin to produce lipids, and (c) recovering the lipids. The lipids obtained with said process can be used in the production of biofuels.

International patent application WO 2010/149859 describes a method for the production of fat, characterized in that the method comprises the following steps: putting a liquid phase or a residual cell mass or a mixture thereof, or a fraction(s) thereof, obtained by separation, before or after the recovery of fat or during the recovery of fat, from a microbial cell mass ("single-cell mass") obtained from a production process of microbial oil ("single-cell oil"), in contact, in a culture medium, with a microorganism capable of producing fat, and allowing the microorganism to produce fat, and/or putting a microbial suspension ("single-cell suspension") or a cell mass obtained from a production process of microbial oil (single-cell oil), or a liquid phase obtained from said process, or a suspension of cells of microorganisms obtained in other ways, a cell mass or a liquid phase obtained in said other ways, or mixtures thereof, or a fraction(s) thus obtained, in contact, in a culture medium, with a microorganism capable of producing fat, and allowing the microorganism to produce fat, and recovering the fat produced or sending the mass of microorganisms to a production process of microbial oil ("single-cell oil"). The fat obtained with said process can be used in the production of biofuels.

American patent application US 2008/0102176 describes a method for the extraction of vegetable fats comprising: pulverizing the raw material containing cellulose in order to obtain particles with a diameter of 1 mm-2 mm; immerging the particles in sulfuric acid at a concentration equal to 1%-2% to acidify said particles in order to increase the hydrolysis of the cellulose and to regulate the pH to a value of 4.5±0.5; removing the particles acidified by the sulfuric acid and adding, in sequence, cellulase and an oleaginous yeast to the acidified particles and subjecting them to fermentation for 8-9 days at a temperature of 25° C.-30° C. and at a humidity of 85%-90%; adding an aliphatic hydrocarbon as solvent to the fermentation products in order to extract the fats obtaining an extraction mixture; removing the acidified particles remaining in the extraction mixture and separating the fats from the solvent by distillation obtaining raw oil. The cellulase is preferably *Trichoderma viride* and the oleaginous yeast is *Rhodotorula glutinis*. The fats obtained can be converted to biodiesel after esterification.

Dai et al. describe the production of biodiesel from oleaginous yeasts in the article: "Biodiesel generation from oleaginous yeast *Rhodotorula glutinis* with xylose assimilating capacity", published in "African Journal of Biotechnology" (2007), Vol. 6 (18), pages 2130-2134. In said article, the lignocellulosic biomass is ground and subjected to acid hydrolysis in the presence of sulfuric acid. The sugars thus obtained are used as carbon sources in a fermentation process in the presence of a previously selected strain of *Rhodotorula glutinis*, capable of also using pentoses, in particular xylose, with the purpose of obtaining oils which are subsequently extracted by Soxhlet extraction and subjected to transesterification in order to obtain biodiesel.

International patent application WO 2010/046051 in the name of the Applicant, describes a process for the production of lipids from biomass including at least one polysaccharide comprising:
  subjecting said biomass to acid hydrolysis in the presence of an aqueous solution of at least one organic acid having from $C_7$ to $C_{20}$ carbon atoms, preferably from $C_9$ to $C_{15}$ carbon atoms, at a temperature ranging from 80° C. to 160° C., preferably ranging from 100° C. to 150° C., obtaining a first mixture comprising a first solid phase and a first aqueous phase;
  subjecting said first mixture to enzymatic hydrolysis obtaining a second mixture comprising a second solid phase and a second aqueous phase;
  subjecting said second aqueous phase to fermentation in the presence of at least one oleaginous yeast obtaining an oleaginous cellular biomass comprising lipids.

The lipids thus obtained can be advantageously used in the production of biodiesel or green diesel which can be used as such, or in a mixture with other automotive fuels.

International patent application WO 2012/052368 in the name of the Applicant, describes a process for the production of lipids from biomass including at least one polysaccharide comprising:
  subjecting said biomass including at least one polysaccharide to acid hydrolysis obtaining a first mixture comprising a first solid phase and a first aqueous phase;
  feeding said first aqueous phase to a fermentation device in the presence of at least one oleaginous yeast obtaining a first fermentation broth comprising a first oleaginous cellular biomass;
  subjecting said first solid phase to acid hydrolysis or enzymatic hydrolysis obtaining a second mixture comprising a second solid phase and a second aqueous phase;
  feeding said second aqueous phase to said fermentation device in the presence of said first fermentation broth obtaining a second fermentation broth comprising a second oleaginous cellular biomass including lipids;
  subjecting at least part of said second fermentation broth to microfiltration obtaining a retentate and a permeate;
  feeding said retentate to said fermentation device.

The lipids thus obtained can be advantageously used in the production of biodiesel or green diesel which can be used as such, or in a mixture with other automotive fuels.

The processes described above, however, can have various drawbacks.

The aqueous phase, for example, which remains at the end of the fermentation (i.e. exhausted fermentation water), which still contains a certain quantity of sugars and of other organic substances such as, for example, acetic acid, glycerol and other small metabolites, and inorganic substances such as, for example, phosphates, nitrates, before being sent to wastewater treatment, must be subjected to pre-treatments in order to abate the organic and inorganic substances contained therein. Consequently, this leads to an increase in the process costs due to both the above pre-treatments of said aqueous phase and also due to the fact that the sugars and other organic and inorganic substances present therein are eliminated without being recovered and used. This can be of little importance in fields wherein the products obtained from the fermentation have a high added value such as, for example, the pharmaceutical or cosmetic industries wherein fermentation processes are often used, but it is of significant importance, on the other hand, in the case of the production of biofuels such as, for example, biodiesel or green diesel, as said biofuels compete with fuels of a fossil origin which have a lower cost.

The Applicant has therefore considered the problem of finding a process for the production of lipids which can be used in the production of biodiesel or green diesel which allows the recovery of the sugars contained in the aqueous phase which remains at the end of the fermentation (i.e. in the exhausted fermentation water) and their recycling to the fermentation.

The Applicant has now found that the production of lipids from biomass including at least one polysaccharide can be advantageously carried out by means of a process which comprises subjecting said biomass including at least one polysaccharide to hydrolysis obtaining a mixture comprising a first solid phase and a first aqueous phase, preparing an inoculum comprising at least one oleaginous microorganism in a first fermentation device obtaining a first fermentation broth, feeding said first aqueous phase and said first fermentation broth to a second fermentation device obtaining a second fermentation broth, subjecting said second fermentation broth to separation obtaining an aqueous suspension of oleaginous cellular biomass comprising lipids and a second aqueous phase, subjecting said second aqueous phase to reverse osmosis obtaining a permeate and a retentate, feeding said retentate to said first fermentation device or to said second fermentation device.

Numerous advantages are obtained by means of said process. Said process, for example, allows the sugars contained in said second aqueous phase remaining at the end of the fermentation to be recovered (i.e. in the exhausted fermentation water) and to be recycled to the fermentation (i.e. to the first fermentation device in order to prepare the inoculum or to the second fermentation device allowing a high yield of lipids). Furthermore, said process allows other organic and inorganic substances which can be used in the fermentation (e.g., nitrates, phosphates) to be recovered and recycled to the same. Said process, moreover, allows lipids to be obtained with a high yield [e.g., a yield of lipids with respect to the total quantity of sugars used for the fermentation higher than or equal to 25%, said yield to lipids being calculated as grams of lipids obtained per gram of sugar used for the fermentation]. Said lipids can be advantageously used in the production of biodiesel or green diesel which can be used as such, or mixed with other automotive fuels.

An object of the present invention therefore relates to a process for the production of lipids from biomass including at least one polysaccharide comprising:
subjecting said biomass including at least one polysaccharide to hydrolysis obtaining a mixture comprising a first solid phase and a first aqueous phase;
preparing an inoculum comprising at least one oleaginous microorganism in a first fermentation device obtaining a first fermentation broth;
feeding said first aqueous phase and said first fermentation broth to a second fermentation device obtaining a second fermentation broth;
subjecting said second fermentation broth to separation obtaining an aqueous suspension of oleaginous cellular biomass comprising lipids and a second aqueous phase;
subjecting said second aqueous phase to reverse osmosis obtaining a permeate and a retentate;
feeding said retentate to said first fermentation device or to said second fermentation device, preferably to said first fermentation device.

For the purposes of the present description and of the following claims, the definition of the numerical ranges always include extremes, unless otherwise specified.

For the purposes of the present description and of the following claims, the term "comprising" also includes the terms "which essentially consists of" or "which consists of".

In accordance with a preferred embodiment of the present invention, said polysaccharide can be selected from cellulose, hemicellulose or mixtures thereof. Cellulose, or mixtures of hemicellulose and cellulose, are particularly preferred.

In accordance with a further preferred embodiment of the present invention, said biomass including at least one polysaccharide is a lignocellulosic biomass. As mentioned above, a lignocellulosic biomass includes three components: hemicellulose, cellulose and lignin.

Preferably, said lignocellulosic biomass may be selected, for example, from:
products of crops expressly cultivated for energy use (for example, miscanthus, foxtail millet, common cane, thistle), including waste products, residues and scraps of said crops or of their processing;
products and by-products of agricultural cultivations, of forestation and of silviculture, comprising wood, plants, residues, mown and waste products of agricultural processings, of forestation and of silviculture;
waste of agro-food products destined for human nutrition or zootechnics;
residues, not chemically treated, of the paper industry;
waste products coming from the differentiated collection of solid urban waste (e.g., urban waste of a vegetable origin, paper).

In accordance with a preferred embodiment of the present invention, said biomass including at least one polysaccharide can be subjected to a preliminary grinding process before being subjected to said hydrolysis. Preferably, said biomass including at least one polysaccharide may be ground until particles having a diameter ranging from 0.1 mm to 10 mm, more preferably ranging from 0.5 mm to 4 mm, are obtained. Particles having a diameter of less than 1 mm are particularly preferred.

For the purposes of the present invention, the hydrolysis of the biomass including at least one polysaccharide can be carried out according to any of the methods known in the art. Non-limiting examples of these methods are:
thermal treatment known as "steam explosion", followed by enzymatic hydrolysis, as described, for example, in international patent application WO 2012/042544 cited above;
treatment in the presence of diluted acids, for example, diluted sulfuric acid, followed by enzymatic hydrolysis, as described, for example, by Humbrid D. et al., in "Technical Report Nrel/Tp-5100-47764 (May 2011);

treatment in the presence of organic acids, for example, 2-naphthalene-sulfonic acid, followed by enzymatic hydrolysis, as described, for example, in international patent application WO 2010/046051 in the name of the Applicant cited above.

Said enzymatic hydrolysis can be carried out according to methods known in the art as described, for example, in American patents U.S. Pat. No. 5,628,830, U.S. Pat. No. 5,916,780 and U.S. Pat. No. 6,090,595, using commercial enzymes such as for example, Celluclast 1.5 L (Novozymes), Econase CE (Rohm Enzymes), Spezyme (Genecor), Novozym 188 (Novozymes), used individually or mixed with each other.

A mixture comprising a solid phase and an aqueous phase is obtained from said hydrolysis. Said mixture is subjected to filtration or centrifugation in order to obtain a first solid phase and a first aqueous phase.

Said first solid phase comprises lignin and said first aqueous phase comprises at least one sugar having from 5 to 6 carbon atoms, more preferably xylose and glucose.

The quantities of sugars obtained after hydrolysis can be determined by means of techniques known in the art such as, for example, High Performance Liquid Chromatography (HPLC), or ion exchange chromatography.

According to a preferred embodiment of the present invention, said first aqueous phase can comprise:
- a quantity of glucose higher than or equal to 100 g/l, preferably higher than or equal to 200 g/l, up to the solubility limit of the glucose in said first aqueous phase;
- from 0 g/l to 200 g/l, preferably from 10 g/l to 100 g/l, of xylose;
- from 0 g/l to 20 g/l, preferably from 5 g/l to 10 g/l, of arabinose;
- from 0 g/l to 20 g/l, preferably from 2 g/l to 10 g/l, of mannose;
- from 0 g/l to 10 g/l, preferably from 2 g/l to 8 g/l, of galactose;
- from 0 g/l to 8 g/l, preferably from 0 g/l to 5 g/l, of acetic acid;
- from 0 g/l to 0.7 g/l, preferably from 0 g/l to 0.5 g/l, of furfural;
- from 0 g/l to 2.5 g/l, preferably from 0 g/l to 2 g/l, of 5-hydroxymethylfurfural.

In order to obtain said inoculum, in addition to at least one oleaginous microorganism, at least one aqueous solution comprising a quantity of sugars higher than or equal to 40 g/l, preferably ranging from 45 g/l to 60 g/l, must be fed to said first fermentation device.

According to the process object of the present invention, said aqueous solution comprising a quantity of sugars higher than or equal to 40 g/l, preferably ranging from 45 g/l to 60 g/l, is the retentate obtained from reverse osmosis.

According to a preferred embodiment of the present invention, in said first fermentation device, the fermentation can be carried out at a temperature ranging from 20° C. to 40° C., preferably ranging from 25° C. to 35° C.

According to a preferred embodiment of the present invention, in said first fermentation device, the fermentation can be carried out for a time ranging from 10 hours to 36 hours, preferably ranging from 12 hours to 26 hours.

According to a preferred embodiment of the present invention, in said first fermentation device, the fermentation can be carried out at a pH ranging from 4.5 to 7, preferably ranging from 5 to 6.7. In order to maintain the pH at the desired ranges, an aqueous solution of at least one inorganic base, such as, for example, sodium hydroxide, potassium hydroxide, calcium hydroxide, magnesium hydroxide, preferably sodium hydroxide, or mixtures thereof, or of at least one organic acid such as, for example, phosphoric acid, sulfuric acid, preferably phosphoric acid, or mixtures thereof, can be added to the culture medium used for the fermentation, in such a quantity so as to obtain the desired pH.

It should be noted, however, that when the process object of the present invention is carried out for the first time, said aqueous solution comprising a quantity of sugars higher than or equal to 40 g/l, preferably ranging from 45 g/l to 60 g/l, can be substituted with an aliquot of the first aqueous phase obtained from the hydrolysis of the biomass including at least one polysaccharide, optionally diluted so as to have the desired quantity of sugars.

When the oleaginous microorganism has reached a concentration higher than or equal to 8 g/l, preferably ranging from 10 g/l to 20 g/l, said first fermentation broth, according to the process object of the present invention, is fed to a second fermentation device.

According to a preferred embodiment of the present invention, in said second fermentation device, the fermentation can be carried out at a temperature ranging from 20° C. to 40° C., preferably ranging from 25° C. to 35° C.

According to a preferred embodiment of the present invention, in said second fermentation device, the fermentation can be carried out for a time ranging from 2 days to 10 days, preferably ranging from 3 days to 8 days.

According to a preferred embodiment of the present invention, in said second fermentation device, the fermentation can be carried out at a pH ranging from 4.5 to 7, preferably ranging from 5 to 6.7. In order to maintain the pH at the desired ranges, an aqueous solution of at least one inorganic base, such as, for example, sodium hydroxide, potassium hydroxide, calcium hydroxide, magnesium hydroxide, preferably sodium hydroxide, or mixtures thereof, or of at least one organic acid such as, for example, phosphoric acid, sulfuric acid, preferably phosphoric acid, or mixtures thereof, can be added to the culture medium used for the fermentation, in such a quantity so as to obtain the desired pH.

According to a preferred embodiment of the present invention, said oleaginous microorganism can be selected from yeasts such as, for example: *Rhodotorula glutinis, Rhodotorula gracilis, Rhodotorula graminis, Lypomyces starkeyi, Lypomyces lipofer, Trigonopsis variabilis, Candida kefyr, Candida curvata, Candida lipolytica, Torulopsis* sp., *Pichia stipitis, Trichosporon cacaoliposimilis, Rhodosporidium* sp., *Cryptococcus curvatus*.

According to a preferred embodiment of the present invention, the fermentation in said second fermentation device can be carried out in one or more steps in batch ("feed-batch fermentation"), semi-continuous or continuous mode. In the case of fermentation with a semi-continuous or continuous culture, there is a continuous addition of nutrients (first aqueous phase) and a optional recycling of the oleaginous cellular biomass after elimination of the exhausted fermentation water (second aqueous phase), for example, by means of microfiltration.

The fermentation is carried out in said first fermentation device and in said second fermentation device, devices known in the art, in the presence of culture mediums normally used for the purpose comprising, in addition to sugars, various nutrients such as, for example, nitrogen, potassium phosphate, magnesium, salts, vitamins, microelements.

In order to deactivate the lipolytic enzymes (e.g., lipase), said second fermentation broth can be subjected, at the end of the fermentation, to thermal treatment. Said thermal treatment can be carried out at a temperature ranging from 70° C. to 120° C., preferably ranging from 75° C. to 110° C., for a time ranging from 5 minutes to 3 hours, preferably ranging from 30 minutes to 2 hours.

The separation to which said second fermentation broth is subjected in order to recover said aqueous suspension of oleaginous cellular biomass comprising lipids (said aqueous suspension of oleaginous cellular biomass having a higher concentration of oleaginous cellular biomass with respect to the concentration of oleaginous cellular biomass in said second fermentation broth) and said second aqueous phase (said second aqueous phase optionally containing suspended solids, for example, cells of the oleaginous microorganism used in the fermentation, or particulate deriving from a deterioration in the equipment used in the process, or from the precipitation of salts), can be carried out using methods known in the art such as, for example, filtration, filter-press, microfiltration or ultrafiltration, centrifugation.

In order to keep the volume of said second fermentation broth constant in said second fermentation device and to increase the concentration of the oleaginous cellular biomass in said second fermentation broth, at least a part of said second fermentation broth, before being subjected to separation, can be subjected to microfiltration obtaining an aqueous phase (permeate) which is joined to said second aqueous phase and sent to reverse osmosis and an oleaginous cellular biomass (retentate) which is sent to said second fermentation device.

According to a preferred embodiment of the present invention, said reverse osmosis can be carried out in the presence of at least one polymeric membrane which can be selected, for example, from polymeric membranes generally used for desalination (usually known as "sea water membranes" or "brakish water membranes") such as, for example: membranes comprising polyamides, polyimides, polysulfones, polyethersulfones. Said polymeric membrane is preferably selected from polymeric membranes comprising polyamides.

According to a preferred embodiment of the present invention, said polymeric membrane can have a maximum operating temperature ranging from 15° C. to 90° C., preferably ranging from 20° C. to 80° C.

According to a preferred embodiment of the present invention, said polymeric membrane can have a maximum operating pressure ranging from 5 bar to 80 bar, preferably ranging from 10 bar to 70 bar.

According to a preferred embodiment of the present invention, said polymeric membrane can have a nominal molecular weight cut-off (MWCO) ranging from 30 daltons to 200 daltons, preferably ranging from 40 daltons to 100 daltons.

According to a preferred embodiment of the present invention, said polymeric membrane can have a maximum operating pH ranging from 1 to 13, preferably ranging from 2 to 11.

Examples of polymeric membranes which can be used for the purposes of the present invention and which are commercially available are the following products: Dow™ Filmtec™ of the series SW30, or of the series BW30, or of the series BW30LE, of Dow Chemical, or the products Desal™ of the series AG, of General Electric, or the products TFC®-HR of Koch Membrane Systems.

The above polymeric membrane can be in the form of flat discs, tubular membranes, spiral module membranes, thin film composite membranes (TFC), or in other useful forms.

According to a preferred embodiment of the present invention, said reverse osmosis can be carried out at a temperature ranging from 5° C. to 90° C., more preferably ranging from 15° C. to 60° C.

According to a preferred embodiment of the present invention, said reverse osmosis can be carried out applying a pressure in the feeding side (retentate side) ranging from 5 bar to 80 bar, more preferably ranging from 10 bar to 40 bar.

According to a preferred embodiment of the present invention, said reverse osmosis can be carried out operating at a specific flow-rate (kg of permeate per square meter of surface of the reverse osmosis membrane per hour) ranging from 5 kg/(m$^2$×h) to 80 kg/(m$^2$×h), more preferably ranging from 10 kg/(m$^2$×h) to 40 kg/(m$^2$×h).

It should be noted that said second aqueous phase which generally has a pH ranging from 4.5 to 7, can be subjected to reverse osmosis without having to adjust the pH.

For the purposes of the present invention and of the following claims, the term "retentate" refers to the aqueous stream concentrated in sugars deriving from said second aqueous phase. Said aqueous stream concentrated in sugars preferably contains a quantity of sugars ranging from 20 g/l to 70 g/l, more preferably ranging from 30 g/l to 60 g/l.

For the purposes of the present invention and of the following claims, the term "permeate" refers to the aqueous stream deriving from said second aqueous phase. Said aqueous stream has a content of organic product, expressed as TOC ("Total Organic Carbon"), determined as described hereunder, lower than or equal to 300 ppm, more preferably ranging from 30 ppm to 150 ppm.

Said total organic carbon (TOC) was determined by combustion using a TOC analyzer capable of determining the total carbon content (TC) and the content of inorganic carbon (IC) from which the content of total organic carbon (TOC) is calculated, by difference.

Said permeate can be subjected to further treatments to allow it to be eliminated, or it can be recovered and used as process water within the process object of the present invention (for example, as washing or diluting water).

In order to eliminate the optional suspended solids present in said second aqueous phase (e.g., cells of the oleaginous microorganism used in the fermentation, or particulate deriving from a deterioration in the equipment used in the process, or from the precipitation of salts), and to protect the reverse osmosis system, before being subjected to reverse osmosis, said second aqueous phase can be subjected to microfiltration or ultrafiltration.

According to a preferred embodiment of the present invention, before being subjected to reverse osmosis, said second aqueous phase can be subjected to microfiltration or ultrafiltration, more preferably microfiltration.

Said microfiltration can be carried out with systems known in the art, for example, by means of cartridge filters generally having a size (i.e. they do not allow the permeation of particles with larger dimensions) of 10 μm, 5 μm, or 1 μm.

Said ultrafiltration can be carried out with systems known in the art, for example, by means of ultrafiltration membranes with a nominal pore diameter within the range of 0.03 μm to 0.1 μm.

In order to increase the yield of lipids, corn steep liquor or corn steep solid can be added to said second fermentation device.

According to a preferred embodiment of the present invention, said process additionally comprises adding corn steep liquor or corn steep solid to said second fermentation device in a quantity preferably ranging from 2 g/l to 20 g/l, more preferably ranging from 4 g/l to 18 g/l.

In order to further concentrate the aqueous suspension of oleaginous cellular biomass comprising lipids obtained after separation, said aqueous suspension of oleaginous cellular biomass, before being subjected to recovery of the lipids (i.e. cell lysis, solvent extraction and evaporation of the solvent), can be subjected to centrifugation. Said centrifugation can be carried out for a time ranging from 5 minutes to 30 minutes, preferably ranging from 15 minutes to 25 minutes, at a rotation rate ranging from 3000 rpm to 9000 rpm, preferably ranging from 4000 rpm to 8000 rpm.

In order to recover the lipids, said aqueous suspension of oleaginous cellular biomass comprising lipids can be subjected to cell lysis which can be carried out by means of various methods. Non-limiting examples of said methods are:
- thermal treatment, which can be carried out using pressurized autoclaves (for example, an autoclave Brignole Mod. AU-2, or a stirred reactor Parr Mod. PA 4575), at a pressure ranging from 2 bar to 6.5 bar, preferably ranging from 3 bar to 5.5 bar, at a temperature ranging from 100° C. to 160° C., preferably ranging from 110° C. to 150° C., for a time ranging from 1 hour to 8 hours, preferably ranging from 1.5 hours to 4 hours, under stirring, ranging from 100 rpm to 800 rpm, preferably ranging from 400 rpm to 600 rpm, as described, for example, in international patent application WO 2012/052368 in the name of the Applicant cited above;
- mechanical treatment, which can be carried out using high-pressure homogenizers (for example, a homogenizer Mod. NS3006L of Gea NiroSoavi), at a pressure ranging from 800 bar to 2000 bar, preferably ranging from 1000 bar to 1600 bar, at a temperature ranging from 10° C. to 100° C., preferably ranging from 20° C. to 80° C., at a flow-rate of the aqueous suspension of oleaginous cellular biomass ranging from 5 l/h to 50 l/h, preferably ranging from 7 l/h to 40 l/h.
- microwave treatment, which can be carried out using microwave equipment (for example, a microwave apparatus Mod. MycroSYNTH of Milestone), at a temperature ranging from 45° C. to 150° C., preferably ranging from 50° C. to 100° C., for a time ranging from 10 minutes to 2 hours, preferably ranging from 15 minutes to 1 hour.

At the end of said cell lysis, the lipids can be recovered from the exhausted aqueous suspension of oleaginous cellular biomass comprising lipids obtained, by means of extraction using, for example, a reflux extractor.

Said extraction can be carried out in the presence of at least one organic solvent which can be selected from apolar organic solvents such as, for example, iso-octane, n-octane, or mixtures thereof; mixtures of hydrocarbons such as, for example, naphtha or diesel cuts which can optionally also derive from the production of green diesel; polar organic solvents such as, for example, methanol, ethanol, iso-propanol, acetone, ethyl acetate, hexane, methyl-tert-butyl ketone, ethyl-tert-butyl ether, or mixtures thereof; or mixtures thereof.

Said extraction can be carried out at a temperature ranging from 20° C. to 200° C., preferably at the boiling point of the solvent used.

Said extraction can be carried out in the presence of a quantity of solvent ranging from 1 to 6 times, preferably ranging from 1.5 times to 5 times, the volume of the aqueous phase of the aqueous suspension of exhausted oleaginous cellular biomass comprising lipids obtained from the cell lysis.

The aqueous suspension of exhausted oleaginous cellular biomass comprising lipids obtained after said cell lysis can be subjected to extraction once or various times. Said aqueous suspension of exhausted oleaginous cellular biomass comprising lipids is preferably subjected to extraction from 1 to 5 times, more preferably from 1 to 3 times.

At the end of the above extraction, the following two phases are obtained:
(i) an organic phase comprising lipids dissolved in solvent;
(ii) an aqueous phase comprising cell debris and traces of non-separated lipids.

In order to recover the lipids, said organic phase (i) is subjected to evaporation, obtaining, as residue, a high-boiling oil (ia) comprising lipids and a liquid phase containing the solvent which can be recycled to the above extraction.

The process object of the present invention allows lipids to be recovered with an extraction yield ranging from 40% to 99.9%, preferably ranging from 45% to 99%, said extraction yield being calculated with respect to the total quantity of lipids present in the oleaginous cellular biomass (dry) obtained after fermentation.

The lipids included in said organic phase (i) are preferably triglycerides, more preferably esters of glycerol with fatty acids having from 14 to 24 carbon atoms such as, for example, palmitic acid, stearic acid, oleic acid, α-linoleic acid, in a quantity higher than or equal to 80% by weight, preferably higher than or equal to 90% by weight, with respect to the total weight of lipids. Other lipids which can be present in said organic phase (i) are: phospholipids, monoglycerides, diglycerides, free fatty acids, or mixtures thereof.

The total quantity of lipids present in the aqueous suspension of oleaginous cellular biomass obtained after fermentation in said second fermentation device, as also the total quantity of lipids contained in said high-boiling oil (ia), can be determined by means of methods known in the art such as, for example, the colorimetric method which is based on the reaction of lipids with phosphoric acid and phospho-vanillin using, for example, the "total lipids-sulpho-phospho vanillin" kit commercialized by Spinreact S.a/S.A.U., Ctra Santa Coloma, 7 E-17176 Sant Esteve de Bas (GI), Spain. Further details relating to this method can be found, for example, in the following article: "Chemical Basis of the Sulpho-phospho-vanillin Reaction for Estimating Total Serum Lipids", J. A. Knight et al., published in "Clinical Chemistry" (1972), Vol. 18, No. 3, pages 199-202.

Said aqueous phase (ii) comprising cell debris, in particular proteins and polysaccharides contained in the cell membrane of the oleaginous microorganism used, can be dehumidified and upgraded as fuel, optionally associated with the lignin deriving from the hydrolysis of the biomass.

Alternatively, said aqueous phase (ii) can be subjected to anaerobic digestion for the production of biogas, which can be used for the production of electric energy, which can also be used for satisfying the energy requirement of the process object of the present invention.

Alternatively, said aqueous phase (ii) can be subjected to liquefaction for the production of bio-oil as described, for example, in international patent applications WO 2010/069583 or WO 2010/069516, in the name of the Applicant.

The lipids obtained according to the process object of the present invention, can be subjected to esterification in the presence of at least one alcohol having from 1 to 4 carbon atoms, preferably methanol, ethanol, and of at least one acid or base catalyst, in order to produce glycerol and alkyl esters, in particular methyl esters or ethyl esters (biodiesel).

Alternatively, said lipids can be subjected to hydrogenation/deoxygenation in the presence of hydrogen and of at least one catalyst in order to produce green diesel. Hydrogenation/deoxygenation processes are known in the art and are described, for example, in European patent application EP 1,728,844.

The present invention will now be illustrated in greater detail by means of an embodiment with reference to FIG. 1 provided hereunder.

Figure 1:
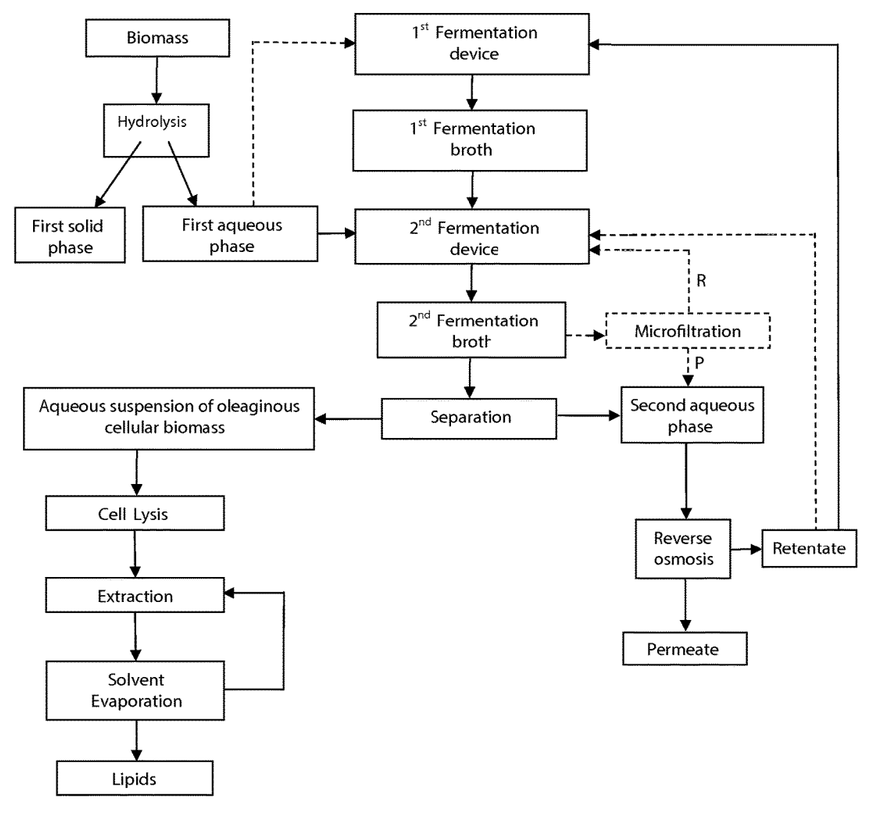

FIG. 1 schematizes an embodiment of the process object of the present invention. For this purpose, the biomass including at least one polysaccharide (e.g., lignocellulosic biomass previously ground) is subjected to hydrolysis (operating according to one of the methods known in the art indicated above) obtaining a mixture comprising a first aqueous phase and a first solid phase including lignin.

Said mixture is subjected to filtration or centrifugation (not represented in FIG. 1) obtaining a first solid phase and a first aqueous phase.

In the meantime, an inoculum is prepared in a first fermentation device using an oleaginous microorganism (e.g., *Rhodotorula graminis, Trichosporon cacaoliposimilis*) obtaining a first fermentation broth: it should be noted that, as mentioned above, the first time that the process object of the present invention is carried out, the aqueous solution comprising a quantity of sugars higher than or equal to 40 g/l, preferably ranging from 45 g/l to 60 g/l, i.e. the retentate, will be substituted by an aliquot of the first aqueous phase obtained from the hydrolysis of the biomass including at least one polysaccharide, optionally diluted so as to have the desired quantity of sugars (indicated in FIG. 1 with the dashed line).

Said first aqueous phase and said first fermentation broth are fed to a second fermentation device in the presence of an oleaginous microorganism (e.g., *Rhodotorula graminis, Trichosporon cacaoliposimilis*) obtaining a second fermentation broth.

Said second fermentation broth is subjected to separation (e.g., by means of centrifugation) obtaining an aqueous suspension of oleaginous cellular biomass and a second aqueous phase.

According to an embodiment of the present invention, at least a part of said second fermentation broth can be subjected to microfiltration obtaining an aqueous phase (permeate—P) which is joined to said second aqueous phase and sent to reverse osmosis and an aqueous suspension of oleaginous cellular biomass (retentate—R) which is sent to said second fermentation device (indicated in FIG. 1 with the dashed line).

Said aqueous suspension of oleaginous cellular biomass is subjected to cell lysis (operating according to one of the methods described above), extraction in the presence of a solvent and subsequent evaporation of the solvent obtaining lipids.

Said second aqueous phase is subjected to reverse osmosis (e.g., using a polymeric membrane comprising polyamide) obtaining a retentate (i.e. aqueous solution comprising a quantity of sugars higher than or equal to 40 g/l) which is fed to said first fermentation device and a permeate (i.e. water having a TOC lower than or equal to 300 mg/l).

Alternatively, said retentate can be fed to said second fermentation device (indicated in FIG. 1 with the dashed line).

Some illustrative and non-limiting examples are provided hereunder for a better understanding of the present invention and for its practical embodiment.

EXAMPLE 1

Composition of the Lignocellulosic Hydrolyzate

The lignocellulosic hydrolyzate (i.e. "first aqueous phase") used in the following examples had the following composition: glucose (126 g/l), xylose (87.1 g/l), arabinose (7.5 g/l), mannose (2.9 g/l), galactose (6.5 g/l), acetic acid (4.9 g/l), furfural (0.46 g/l), 5-hydroxymethylfurfural (1.85 g/l), for a total sugar content equal to 230 g/l.

The content of furfural and of 5-hydroxymethylfurfural was determined by means of High Performance Liquid Chromatography (HPLC) using a LichroCART Purospher RP-18 end-capped column (240 mm×mm; 5 μm) of Merck, equipped with a photodiode UV detector, with a flow of 0.8 ml/min, temperature 40° C., and with phosphoric acid mobile phase at 0.05% in water (eluent A) and acetonitrile+ phosphoric acid at 0.05% in water, in a ratio of 90/10 vol/vol (eluent B), using the elution gradient indicated in Table 1.

TABLE 1

| Time (min) | Eluent A (%) | Eluent B (%) |
| --- | --- | --- |
| 0 | 100 | 0 |
| 4 | 94 | 6 |
| 30 | 85 | 15 |

The sugar content was determined by means of ion-exchange chromatography (HPAE-PAD), using a Dionex chromatograph, equipped with a Carbopac PA100 column, with a gradient of sodium hydroxide and sodium acetate as counter-ion.

The quantitative determination of the organic acids, i.e. acetic acid, was carried out by means of a DIONEX BIOLC 4000 ion chromatograph coupled with a Pulsed Electrochemical Detector (PED), an Ice-AS1 chromatographic column (diameter: 9 mm; length: 250 mm), an AMMS-ICE (Anion MicroMembrane Suppressor), injection volume 50 μl, elution in isocratic mode with heptafluorobutyric acid 0.4 mM as eluent.

EXAMPLE 2

Preparation of Inoculum with Hydrolyzate (*Rhodotorula Graminis*)

As the retentate obtained from the reverse osmosis according to the process, object of the present invention, was not yet available, the inoculum (i.e. first fermentation broth) was prepared using part of the lignocellulosic hydrolyzate (i.e. first aqueous phase) described in Example 1.

For this purpose, 19.4 ml of said lignocellulosic hydrolyzate (i.e. first aqueous phase) suitably diluted with water (80.6 ml) so as to have a final concentration of sugars equal to 44.5 g/l, were introduced into a 500 ml flask, equipped with a magnetic stirrer, to which 10 g/l of yeast extract and g/l of peptone were subsequently added: the pH of the mixture obtained was brought to 6 by the addition of a few drops of potassium hydroxide (KOH) 2.5 M. The mixture obtained was sterilized in an autoclave at 80° C., for 45 minutes.

At the end of the sterilization, the mixture obtained was brought to room temperature (25° C.) and inoculated with cells of *Rhodotorula graminis* DBVPG 4620 which were left to grow, for 24 hours, at 30° C., under stirring (200 rpm), until a first fermentation broth was obtained, having a concentration of oleaginous cellular biomass equal to 13.32 g/l (dry weight).

EXAMPLE 3

Fermentation of *Rhodotorula graminis* (Feed-Batch Mode)

The fermentation test with cells of *Rhodotorula graminis* DBVPG 4620 was carried out in feed-batch mode in a 20 liter fermenter, operating under the following conditions:
- 2.6 l of lignocellulosic hydrolyzate (i.e. first aqueous phase) described in Example 1, suitably diluted with water so as to have an initial sugar concentration equal 100 g/l;
- 1.0 g/l of yeast extract;
- 2.5 g/l of corn steep solid;
- 2.5 g/l of $(NH_4)_2SO_4$;
- 1 g/l of $KH_2PO$;
- 0.05 g/l of $MgSO_4.7H_2O$;
- 0.01 g/l of NaCl;
- 0.01 g/l of $CaCl_2.2H_2O$;
- air fed: flow equal to 1 l/min;
- operating pH equal to 6, maintained by the addition, when necessary, of a few drops of a solution of potassium hydroxide (KOH) 5 M and phosphoric acid ($H_3PO_4$) 10% (v/v);
- stirring equal to 600 rpm-900 rpm, modulated with the air flow so as to maintain the concentration of dissolved oxygen ($DO_2$) above 30%;
- initial volume: 6 liters;
- inoculum of *Rhodotorula graminis* DBVPG 4620 (i.e. first fermentation broth) obtained as described in Example 2, diluted at 10% (v/v) with the culture medium used for the fermentation, in order to start the fermentation with a concentration of oleaginous cellular biomass equal to 1.3 g/l (dry weight).

The fermentation was carried out batchwise for the first 36 hours obtaining a fermentation broth having a concentration of oleaginous cellular biomass equal to 29.03 g/l (dry weight) and a residual concentration of sugars equal to 38.5 g/l.

Additions were subsequently made to the fermentation broth, operating in feed-batch mode of lignocellulosic hydrolyzate (i.e. first aqueous phase) described in Example 1, suitably diluted with water so as to have a total concentration of sugars equal to 199.71 g/l: in particular, three additions were made, two of 1 liter each, after 36 hours and after 54 hours of fermentation respectively, and one of 2 liters after 44 hours of fermentation.

At the end of the fermentation, after 122 hours, a second fermentation broth was obtained, having a concentration of oleaginous cellular biomass equal to 62.62 g/l (dry weight) and a content of total lipids equal to 60% by weight with respect to the dry weight of said oleaginous cellular biomass.

Said second fermentation broth was subjected to separation by means of centrifugation at 7000 rpm, for 20 minutes obtaining 2.1 kg of oleaginous cellular biomass [626 g (dry weight)–concentration equal to 30% by weight with respect to the total quantity of oleaginous cellular biomass obtained] having a content of total lipids equal to 60% by weight with respect to the dry weight of said oleaginous cellular biomass and 7.9 l of exhausted fermentation water (i.e. second aqueous phase) having a content of non-metabolized sugars equal to 15.15 g/l.

The total lipid content was determined using the "total lipids-sulpho-phospho vanillin" kit, operating as described above. The sugar content was determined operating as described in Example 1.

A yield of oleaginous cellular biomass was reached with respect to the substrate consumed ($Y_{X/S}$=g of biomass obtained per g of substrate consumed) equal to 0.41 g/g, and a yield of lipids with respect to the substrate consumed ($Y_{L/S}$=g of lipids obtained per g of substrate consumed) equal to 0.25 g/g.

EXAMPLE 4

Preparation of Inoculum with Lignocellulosic Hydrolyzate (*Trichosporon cacaoliposimilis*)

As the retentate obtained from the reverse osmosis according to the process object of the present invention, was not yet available, the inoculum was prepared using part of the lignocellulosic hydrolyzate (i.e. first aqueous phase) described in Example 1.

For this purpose, 19.4 ml of said lignocellulosic hydrolyzate (i.e. first aqueous phase) suitably diluted with water (80.6 ml) so as to have a final concentration of sugars equal to 44.5 g/l, were introduced into a 500 ml flask, equipped with a magnetic stirrer, to which 10 g/l of yeast extract and g/l of peptone were subsequently added: the pH of the mixture obtained was brought to 6 by the addition of a few drops of potassium hydroxide (KOH) 2.5 M. The mixture obtained was sterilized in an autoclave at 80° C., for 45 minutes.

At the end of the sterilization, the mixture obtained was brought to room temperature (25° C.) and inoculated with cells of *Trichosporon cacaoliposimilis* ATCC 20509 which were left to grow, for 24 hours, at 30° C., under stirring (200 rpm), until a first fermentation broth was obtained, having a concentration of oleaginous cellular biomass equal to 15.7 g/l (dry weight).

EXAMPLE 5

Fermentation of *Trichosporon cacaoliposimilis* (Feed-Batch Mode)

The fermentation test with cells of *Trichosporon cacaoliposimilis* ATCC 20509 was carried out in feed-batch mode in a 20 liter fermenter, operating under the following conditions:
- 2.6 l of lignocellulosic hydrolyzate described in Example 1, suitably diluted with water so as to have an initial sugar concentration equal 100 g/l;
- 1.0 g/l of yeast extract;
- 2.5 g/l of corn steep solid;
- 2.5 g/l of $(NH_4)_2SO_4$;
- 1 g/l of $KH_2PO$;
- 0.05 g/l of $MgSO_4.7H_2O$;
- 0.01 g/l of NaCl;
- 0.01 g/l of $CaCl_2.2H_2O$;
- air fed: flow equal to 1 l/min;
- operating pH equal to 6, maintained by the addition, when necessary, of a few drops of a solution of potassium hydroxide (KOH) 5 M and phosphoric acid ($H_3PO_4$) 10% (v/v);
- stirring equal to 600 rpm-900 rpm, modulated with the air flow so as to maintain the concentration of dissolved oxygen ($DO_2$) above 30%;
- initial volume: 6 liters;
- inoculum of *Trichosporon cacaoliposimilis* ATCC 20509 (i.e. first fermentation broth) obtained as described in Example 4, diluted at 10% (v/v) with the culture medium used for the fermentation, in order to start the fermentation with a concentration of oleaginous cellular biomass equal to 1.6 g/l (dry weight).

The fermentation was carried out batchwise for the first 30 hours obtaining a fermentation broth having a concentration of oleaginous cellular biomass equal to 24.1 g/l (dry weight) and a residual concentration of sugars equal to 38.5 g/l.

Additions were subsequently made to the fermentation broth, operating in feed-batch mode of the lignocellulosic hydrolyzate (i.e. first aqueous phase) obtained as described in Example 4, suitably diluted with water so as to have a concentration of sugars equal to 199.71 g/l: in particular, four additions were made, three of 2 liters each, after 30 hours, after 40 hours and after 53 hours of fermentation respectively, and one of 3 liters after 47 hours of fermentation.

At the end of the fermentation, after 60 hours, a second fermentation broth was obtained, having a concentration of oleaginous cellular biomass equal to 77.12 g/l (dry weight) and a content of total lipids equal to 54% by weight with respect to the dry weight of said oleaginous cellular biomass.

Said second fermentation broth was subjected to separation by means of centrifugation at 7000 rpm, for minutes obtaining 3.9 kg of oleaginous cellular biomass [1157 g (dry weight)–concentration equal to 30% by weight with respect to the total quantity of oleaginous cellular biomass obtained] having a content of total lipids equal to 54% by weight with respect to the dry weight of said oleaginous cellular biomass and 11 l of exhausted fermentation water (i.e. second aqueous phase) having a content of non-metabolized sugars equal to 2.8 g/l.

The total lipid content was determined using the "total lipids-sulpho-phospho vanillin" kit, operating as described above. The sugar content was determined operating as described in Example 1.

A yield of oleaginous cellular biomass was reached with respect to the substrate consumed ($Y_{X/S}$=g of biomass obtained per g of substrate consumed) equal to 0.42 g/g, and a yield of lipids with respect to the substrate consumed ($Y_{L/S}$=g of lipids obtained per g of substrate consumed) equal to 0.21 g/g.

EXAMPLE 6

Concentration of Fermentation Water by Means of Reverse Osmosis

The test was carried out using an apparatus for tests with flat membranes, consisting of a cylindrical steel container, on whose base the polymeric membrane was assembled on a filtering porous septum, forming the support for the membrane. The container, equipped with stirring, can be pressurized with air or inert gas up to a pressure of 35 bar. The permeate filtered through the membrane and was collected in an underlying container, whereas the retentate remained inside the container.

The membrane BW30 of Dow Chemical was used for the concentration of the fermentation water, which is a thin film composite membrane (TFC) based on polyamide, having the following characteristics:
nominal molecular weight cut-off (MWCO)=50 Daltons;
operating pH=2-11;
maximum operating temperature=70° C.;
maximum operating pressure=68 bar.

For this purpose, at the end of the fermentation, the second fermentation broth, obtained as described in Example 3, was subjected, as indicated above, to centrifugation at 7000 rpm, for 20 minutes obtaining 2.1 kg of oleaginous cellular biomass and 7.9 l of exhausted fermentation water (i.e. second aqueous phase).

450 ml of said exhausted fermentation water (i.e. second aqueous phase) were subjected to filtration on a Millipore GF/C filter made of fibreglass, having a porosity of 0.22 μm, and were charged into the apparatus for reverse osmosis described above, under stirring at 500 rpm, at an initial pressure of 15 bar, progressively increased up to 35 bar: the test was carried out at room temperature (25° C.)

The exhausted fermentation water (i.e. second aqueous phase) had the following composition:
total sugars: 15.15 g/l;
furfural: 458 ppm;
5-hydroxymethylfurfural: 711 ppm;
conductivity: 10.5 mS/cm;
TOC: 14300 ppm;
pH: 5.92.

At the end of the reverse osmosis, 120 ml of retentate were recovered, having the following composition:
total sugars: 47.2 g/l;
furfural: 873 ppm;
5-hydroxymethylfurfural: 1915 ppm;
conductivity: 19 mS/cm;
TOC: 52000 ppm;
pH: 5.85.

During the reverse osmosis, a permeate was also recovered. After collecting 225 ml of permeate, equal to a 50% recovery (225 ml of permeate with respect to 450 ml of initial feed), a further 103.5 ml of permeate, were collected, bringing the overall recovery to 73%. The permeate relating to the recovery fraction between 50% and 73%, had the following composition:
total sugars: 0.1063 g/l;
furfural: 376 ppm;
5-hydroxymethylfurfural: 343 ppm;
conductivity: 0.30 mS/cm;
TOC: 140 ppm;
pH: 5.5.

From the above data, it can be deduced that the reverse osmosis allows a concentration factor equal to 3.1 to be obtained for the sugars, 1.9 for the furfural and 2.7 for the 5-hydroxymethylfurfural, with rejection indexes of 0.996 for the sugars, 0.395 for the furfural and 0.670 for the 5-hydroxymethylfurfural, respectively. Said data clearly indicate that the sugars are completely withheld by the membrane and concentrated, whereas the furfural and 5-hydroxymethylfurfural are withheld less and are partly distributed in the permeate. Furthermore, the permeate has a TOC equal to 140 ppm, which corresponds to 560 ppm of COD (COD=TOC×4): the value slightly exceeds the sewage discharge limit without treatment (i.e. COD equal to 500 ppm) and consequently a significant reduction in the treatment costs and water disposal costs is obtained, should it be eliminated. Alternatively, as specified above, said water can be used as process water within the process object of the present invention (for example, as washing or diluting water).

The content of sugars, furfural and 5-hydroxymethylfurfural was determined, operating as described in Example 1. The TOC was determined operating as described above.

EXAMPLE 7

Preparation of Inoculum with Retentate (*Rhodotorula Graminis*)

The retentate obtained as described in Example 6 was used for the preparation of an inoculum (i.e. first fermentation broth).

For this purpose, 100 ml of retentate were introduced into a 500 ml flask, equipped with stirring, to which 10 g/l of yeast extract and 10 g/l of peptone were subsequently added: the pH of the mixture obtained was maintained at 5.85 by the addition of a few drops of potassium hydroxide (KOH) 2.5 M. The mixture obtained was sterilized by filtration on Millipore Stericap® Plus 0.2 μm filters.

The sterilized mixture was inoculated with cells of *Rhodotorula graminis* DBVPG 4620 which were left to grow, for 24 hours, at 30° C., under stirring (200 rpm), obtaining a first fermentation broth having a concentration of oleaginous cellular biomass equal to 8.21 g/l (dry weight).

EXAMPLE 8

Fermentation of *Rhodotorula graminis* (Feed-Batch Mode)] Using the Inoculum Prepared with the Retentate The fermentation test with cells of *Rhodotorula graminis* DBVPG 4620 was carried out in feed-batch mode in a 20 liter fermenter, operating under the following conditions:
- 2.6 l of lignocellulosic hydrolyzate (i.e. first aqueous phase) described in Example 1, suitably diluted with water so as to have an initial sugar concentration equal 100 g/l;
- 1.0 g/l of yeast extract;
- 2.5 g/l of corn steep solid;
- 2.5 g/l of $(NH_4)_2SO_4$;
- 1 g/l of $KH_2PO$;
- 0.05 g/l of $MgSO_4.7H_2O$;
- 0.01 g/l of NaCl;
- 0.01 g/l of $CaCl_2.2H_2O$;
- air fed: flow equal to 1 l/min;
- operating pH equal to 6, maintained by the addition, when necessary, of a few drops of a solution of potassium hydroxide (KOH) 5 M and phosphoric acid ($H_3PO_4$) 10% (v/v);
- stirring equal to 600 rpm-900 rpm, modulated with the air flow so as to maintain the concentration of dissolved oxygen ($DO_2$) above 30%;
- initial volume: 6 liters;
- inoculum of *Rhodotorula graminis* DBVPG 4620 (i.e. first fermentation broth) obtained as described in Example 6, diluted at 10% (v/v) with the culture medium used for the fermentation, in order to start the fermentation with a concentration of oleaginous cellular biomass equal to 1.4 g/l (dry weight).

The fermentation was carried out batchwise for the first 24 hours obtaining a fermentation broth having a concentration of oleaginous cellular biomass equal to 12.07 g/l (dry weight) and a residual concentration of sugars equal to 23.5 g/l.

Additions were subsequently made to the fermentation broth, operating in feed-batch mode of the hydrolyzate obtained as described in Example 1, suitably diluted with water so as to have a total concentration of sugars equal to 199.71 g/l: in particular, three additions were made, two of 1 liter each after 24 hours and after 34 hours of fermentation respectively, and one of 4 liters after 44 hours of fermentation.

At the end of the fermentation, after 144 hours, a second fermentation broth was obtained, having a concentration of oleaginous cellular biomass equal to 57.14 g/l (dry weight) and a content of total lipids equal to 54% by weight with respect to the dry weight of said oleaginous cellular biomass.

Said second fermentation broth was subjected to separation by means of centrifugation at 7000 rpm, for minutes obtaining 2.3 kg of oleaginous cellular biomass [686 g (dry weight)–concentration equal to 30% by weight with respect to the total quantity of oleaginous cellular biomass obtained] having a content of total lipids equal to 54% by weight with respect to the dry weight of said oleaginous cellular biomass and 9.7 l of exhausted fermentation water (i.e. second aqueous phase) having a content of non-metabolized sugars equal to 15.15 g/l.

The total lipid content was determined using the "total lipids-sulpho-phospho vanillin" kit, operating as described above. The sugar content was determined operating as described in Example 1.

A yield of oleaginous cellular biomass was reached with respect to the substrate consumed ($Y_{X/S}$=g of biomass obtained per g of substrate consumed) equal to 0.48 g/g, and a yield of lipids with respect to the substrate consumed ($Y_{L/S}$=g of lipids obtained per g of substrate consumed) equal to 0.26 g/g.

If the retentate obtained as described in Example 6 were not used, the actual fermentation yields, considering the total sugars, would be $Y_{X/S}$ 0.43 g/g and $Y_{L/S}$ 0.23 g/g.

EXAMPLE 9

Recovery of Lipids by Means of Cell Lysis (Thermal Treatment)

For this purpose, at the end of the fermentation, 1180 ml of the second fermentation broth obtained as described in Example 8, having a concentration of oleaginous cellular biomass equal to 57.14 g/l (dry weight), were subjected to centrifugation at 7000 rpm, for 20 minutes, obtaining 200 ml of an aqueous suspension of oleaginous cellular biomass having a concentration of oleaginous cellular biomass equal to 336 g/l (dry weight) and 980 ml of exhausted fermentation water (i.e. second aqueous phase).

The 200 ml of said aqueous suspension were introduced into an 0.5 l autoclave (Parr stirred reactor model PA 4575 A) which was brought to a temperature of 140° C., an autogenous pressure of 4.9 bar, with a stirring of 450 rpm, and kept under these conditions for 2 hours. After this period, the exhausted oleaginous cellular biomass was discharged and sent to the extraction process (Example 12).

EXAMPLE 10

Recovery of Lipids by Means of Cell Lysis (Mechanical Treatment)

For this purpose, at the end of the fermentation, 6 of the second fermentation broth obtained as described in Example 8, having a concentration of oleaginous cellular biomass equal to 57.14 g/l (dry weight), were subjected to centrifugation at 7000 rpm, for 20 minutes, obtaining 1 l of an aqueous suspension of oleaginous cellular biomass having a concentration of oleaginous cellular biomass equal to 336 g/l (dry weight) and 5 l of exhausted fermentation water (i.e. second aqueous phase).

The 1 l of said aqueous suspension were pumped into a homogenizer (Mod. NS3006L of Gea NiroSoavi) at a homogenization pressure of 1500 bar, at room temperature and at a flow-rate of about 15 l/h.

At the end of the treatment, the exhausted oleaginous cellular biomass was discharged and sent to the extraction process (Example 12).

EXAMPLE 11

Recovery of Lipids by Means of Cell Lysis (Microwave Treatment)

For this purpose, at the end of the fermentation, 1180 ml of the second fermentation broth obtained as described in Example 8, having a concentration of oleaginous cellular biomass equal to 57.14 g/l (dry weight), were subjected to centrifugation at 7000 rpm, for 20 minutes, obtaining 200 ml of an aqueous suspension of oleaginous cellular biomass having a concentration of oleaginous cellular biomass equal to 336 g/l (dry weight) and 980 ml of exhausted fermentation water (i.e. second aqueous phase).

The 200 ml of said aqueous suspension were introduced into a 300 ml glass flask equipped with a cooler and a magnetic anchor and were brought to a temperature of 100° C. by means of a microwave device (Mod. "MicroSYNTH" of Milestone). The temperature was kept constant for 20 minutes at atmospheric pressure.

At the end of the treatment, the exhausted oleaginous cellular biomass was discharged and sent to the extraction process (Example 12).

EXAMPLE 12

Solvent Extraction

In order to recover the lipids contained in the oleaginous cellular biomass obtained after the treatments described in Examples 9, 10 and 11, various extraction tests were carried out, using different types of solvents or mixtures thereof.

For this purpose, 200 ml of the aqueous suspension of exhausted oleaginous cellular biomass, obtained as described in Example 9, Example 10, or Example 11, were used in the various tests.

Said aqueous suspension was subjected to two extraction cycles, of 2 hours each, at the boiling point of the solvent or of the mixture of solvents used, in a reflux extractor, in the presence of a volume of solvent or of mixture of solvents equal to twice the volume of said aqueous suspension.

The lipids were obtained after separating the organic phase containing the solvent and lipids from said aqueous suspension containing the exhausted oleaginous cellular biomass, and subjecting said organic phase to distillation of the solvent, which is recycled to the extraction.

The solvents and the mixtures of solvents used, the treatments to which the oleaginous cellular biomass was subjected (Examples 9-11—cell lysis), the extraction temperatures and the extraction yields, are indicated in Table 2.

TABLE 2

| Treatment | Treatment conditions | Extraction solvent | Extraction temperature | Extraction yield* (%) |
|---|---|---|---|---|
| Thermal | autoclave, 140° C., 2 hours | hexane/iso-propanol (3:2; v/v) | 60° C. | 98% |
| Thermal | autoclave, 140° C., 2 hours | ethyl acetate | 72° C. | 95% |
| Thermal | autoclave, 140° C., 2 hours | iso-octane | 82° C. | 74% |
| Thermal | autoclave, 140° C., 2 hours | xylene | 93° C. | 87% |
| Thermal | autoclave, 140° C., 2 hours | ethyl tert-butyl ether | 68° C. | 83% |
| Thermal | autoclave, 140° C., 2 hours | methyl iso-butyl ketone | 90° C. | 97% |
| Thermal | autoclave, 140° C., 2 hours | iso-octane + 10% ethanol | 70° C. | 82% |
| Mechanical | homogenizer, 1500 bar, 15 l/h | ethyl acetate | 72° C. | 71% |
| Microwave | microwave reactor, 100° C., 20 min. | ethyl acetate | 72° C. | 80% |

*the extraction yield (%) is indicated, of lipids obtained from the extraction, with respect to the total quantity of lipids present in the oleaginous cellular biomass (dry) obtained after fermentation determined using the "total lipids-sulpho-phospho vanillin" kit, operating as described above.

The invention claimed is:

1. A process for the production of lipids from biomass including at least one polysaccharide, comprising:
    subjecting said biomass including at least one polysaccharide to hydrolysis obtaining a mixture comprising a first solid phase and a first aqueous phase;
    separating said first aqueous phase from said mixture:
    preparing an inoculum comprising at least one oleaginous microorganism in a first fermentation device obtaining a first fermentation broth;
    feeding said first aqueous phase and said first fermentation broth to a second fermentation device obtaining a second fermentation broth;
    subjecting said second fermentation broth to separation obtaining an aqueous suspension of oleaginous cellular biomass comprising lipids and a second aqueous phase;
    subjecting said second aqueous phase to reverse osmosis obtaining a permeate and a retentate;
    feeding said retentate to said first fermentation device or to said second fermentation device.

2. The process for the production of lipids from biomass including at least one polysaccharide according to claim 1, wherein said polysaccharide is selected from cellulose, hemicellulose, or mixtures thereof.

3. The process for the production of lipids from biomass including at least one polysaccharide according to claim 1, wherein said biomass including at least one polysaccharide is a lignocellulosic biomass.

4. The process for the production of lipids from biomass including at least one polysaccharide according to claim 1, wherein said biomass including at least one polysaccharide is subjected to a preliminary grinding process before being subjected to said hydrolysis.

5. The process for the production of lipids from biomass including at least one polysaccharide according to claim 1, wherein said first aqueous phase comprises;
    an amount of glucose higher than or equal to 100 g/l up to the solubility limit of the glucose in said first aqueous phase;
    from 0 g/l to 200 g/l of xylose;
    from 0 g/l to 20 g/l of arabinose;
    from 0 g/l to 20 g/l of mannose;
    from 0 g/l to 10 g/l of galactose;
    from 0 g/l to 8 g/l of acetic acid;
    from 0 g/l to 0.7 g/l of furfural; and
    from 0 g/l to 2.5 g/l of 5-hydroxymethylfurfural.

6. The process for the production of lipids from biomass including at least one polysaccharide according to claim 1, wherein said retentate is an aqueous solution comprising an amount of sugars higher than or equal to 40 g/l.

7. The process for the production of lipids from biomass including at least one polysaccharide according to claim 1, wherein, in said first fermentation device, the fermentation is carried out at a temperature ranging from 20° C. to 40° C., for a time ranging from 10 hours to 36 hours, at a pH ranging from 4.5 to 7.

8. The process for the production of lipids from biomass including at least one polysaccharide according to claim 1, wherein, in said second fermentation device, the fermentation is carried out at a temperature ranging from 20° C. to 40° C., for a time ranging from 2 days to 10 days, at a pH ranging from 4.5 to 7.

9. The process for the production of lipids from biomass including at least one polysaccharide according to claim 1, wherein said oleaginous microorganism is selected from the following yeasts: *Rhodotorula glutinis, Rhodotorula gracilis, Rhodotorula graminis, Lypomices starkeyi, Lypomices*

*lipofer, Trigonopsis variabilts, Candida kefyr, Candida curvata, Candida lipolytica, Torulopsis* sp., *Pichia stipitis, Trichosporon cacaoliposimilis, Rhodosporidium* sp., *Cryptococcus curvatus.*

10. The process for the production of lipids from biomass including at least one polysaccharide according to claim 1, wherein the fermentation in said second fermentation device is carried out in one or more steps in a mode selected from the group consisting of batch, semi-continuous, continuous, and combinations thereof.

11. The process for the production of lipids from biomass including at least one polysaccharide according to claim 1, wherein said reverse osmosis is carried out in the presence of at least one polymeric membrane selected from polymeric membranes generally used for desalination.

12. The process for the production of lipids from biomass including at least one polysaccharide according to claim 11, wherein said polymeric membrane has a maximum operating temperature ranging from 15° C. to 90° C., a maximum operating pressure ranging from 5 bar to 80 bar, a nominal molecular weight cut-off ranging from 30 daltons to 200 daltons, a maximum operating pH ranging from 1 to 13.

13. The process for the production of lipids from biomass including at least one polysaccharide according to claim 1, wherein said reverse osmosis is carried out at a temperature ranging from 5° C. to 90° C.

14. The process for the production of lipids from biomass including at least one polysaccharide according to claim 1, wherein said reverse osmosis is carried out applying a pressure at the retentate side ranging from 5 bar to 80 bar.

15. The process for the production of lipids from biomass including at least one polysaccharide according to claim 1, wherein said reverse osmosis is carried out operating at a specific flow-rate ranging from 5 kg/(m$^2$×h) to 80 kg/(m$^2$×h).

16. The process for the production of lipids from biomass including at least one polysaccharide according to claim 1, wherein, before being subjected to reverse osmosis, said second aqueous phase, is subjected to microfiltration or ultrafiltration.

17. The process for the production of lipids from biomass including at least one polysaccharide according to claim 1, wherein said process comprises adding corn steep liquor or corn steep solid to said second fermentation device in an amount ranging from 2 g/l to 20 g/l.

\* \* \* \* \*